US012734347B2

(12) United States Patent
Schweikert et al.

(10) Patent No.: US 12,734,347 B2
(45) Date of Patent: Sep. 15, 2026

(54) VENOUS ACCESS PORT WITH MOLDED AND/OR RADIOPAQUE INDICIA

(71) Applicant: Medical Components, Inc., Harleysville, PA (US)

(72) Inventors: Timothy M. Schweikert, West Chester, PA (US); Raymond R. Bizup, Feasterville, PA (US); Kevin E. Sanford, Chalfont, PA (US); Kenneth M. Zinn, Westport, CT (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 18/615,101

(22) Filed: Mar. 25, 2024

(65) Prior Publication Data

US 2024/0226524 A1 Jul. 11, 2024

Related U.S. Application Data

(60) Continuation of application No. 17/865,449, filed on Jul. 15, 2022, now Pat. No. 11,938,296, which is a (Continued)

(51) Int. Cl.
*A61M 39/02* (2006.01)
*A61M 5/00* (2006.01)

(52) U.S. Cl.
CPC ........ *A61M 39/0208* (2013.01); *A61M 5/007* (2013.01); *A61M 2039/0205* (2013.01);

(Continued)

(58) Field of Classification Search
CPC .............. A61M 39/0208; A61M 5/007; A61M 2039/0205; A61M 2039/0229;

(Continued)

(56) References Cited

U.S. PATENT DOCUMENTS

| | | | |
|---|---|---|---|
| 574,387 | A | 1/1897 | Buckler |
| 611,357 | A | 9/1898 | Dembinski |

(Continued)

FOREIGN PATENT DOCUMENTS

| | | |
|---|---|---|
| DE | 8437873 U1 | 3/1986 |
| DE | 3447202 A1 | 7/1986 |

(Continued)

OTHER PUBLICATIONS

International Application No. PCT/US2007/011015, Written Opinion, dated Jun. 10, 2008, 3 pages.

(Continued)

*Primary Examiner* — James D Ponton
*Assistant Examiner* — Hong-Van N Trinh
(74) *Attorney, Agent, or Firm* — John E. Boyd; Fisher Broyles LLP

(57) ABSTRACT

A venous access port assembly having a base, a peripheral surface, and a septum. The base defines an interior reservoir. The peripheral surface includes integrally molded X-ray discernable indicia identifying that the assembly is rated for power injection. The X-ray discernable indicia may extend through a height of the peripheral surface from a top surface to a bottom surface thereof. According to one aspect, the peripheral surface may be formed from X-ray discernable material, and the X-ray discernable indicia may be formed from the X-ray discernable material, or they may be formed by voids in the X-ray discernable material. According to another aspect, the peripheral surface may be formed from a radiotransparent or radiolucent material and applied with a radiopaque agent, and the X-ray discernable indicia may be one or more voids in the radiopaque agent or may be portions of the peripheral surface applied with the radiopaque agent.

19 Claims, 5 Drawing Sheets

Related U.S. Application Data continuation of application No. 16/035,879, filed on Jul. 16, 2018, now Pat. No. 11,406,808, which is a division of application No. 15/350,273, filed on Nov. 14, 2016, now Pat. No. 11,478,622, which is a continuation of application No. 13/550,745, filed on Jul. 17, 2012, now Pat No. 9,533,133, which is a continuation of application No. 12/143,377, filed on Jun. 20, 2008, now Pat. No. 8,257,325.

(60) Provisional application No. 60/936,491, filed on Jun. 20, 2007.

(52) U.S. Cl.
CPC .............. *A61M 2039/0229* (2013.01); *A61M 2039/0238* (2013.01); *A61M 2205/32* (2013.01)

(58) Field of Classification Search
CPC ...... A61M 2039/0238; A61M 2205/32; A61M 39/02–39/0693
See application file for complete search history.

(56) References Cited

U.S. PATENT DOCUMENTS 966,696 A 8/1910 Merrill
D44,302 S 7/1913 Director
1,713,267 A 5/1929 Crowley
2,029,553 A 2/1936 Bartschi
D130,852 S 12/1941 Rothschild
2,433,480 A 12/1947 Rendich
2,891,689 A 6/1959 Gould
D198,453 S 6/1964 Weichselbaum
3,168,070 A 2/1965 Verney, III
3,293,663 A 12/1966 Cronin
3,341,417 A 9/1967 Sinaiko
3,447,202 A 6/1969 Kato
3,518,428 A 6/1970 Jack
3,529,633 A 9/1970 Vaillancourt
3,631,563 A 1/1972 Snowden
3,643,358 A 2/1972 Morderosian
3,829,904 A 8/1974 Ling
3,831,583 A 8/1974 Edmunds
3,840,009 A 10/1974 Michaels
3,878,962 A 4/1975 Holbrook
3,891,997 A 7/1975 Herbert
3,915,162 A 10/1975 Miller
3,919,724 A 11/1975 Sanders
3,922,726 A 12/1975 Trentani
3,951,147 A 4/1976 Tucker
4,027,391 A 6/1977 Samis
4,035,653 A 7/1977 Karasko
4,121,108 A 10/1978 Manor
4,123,806 A 11/1978 Amstutz
4,168,586 A 9/1979 Samis
4,181,132 A 1/1980 Parks
4,190,040 A 2/1980 Schulte
4,190,057 A 2/1980 Downie
4,194,122 A 3/1980 Mitchell
4,202,349 A 5/1980 Jones
4,222,374 A 9/1980 Sampson
4,233,964 A 11/1980 Jefferts
4,274,006 A 6/1981 Caine
4,349,498 A 9/1982 Ellis
4,361,153 A 11/1982 Slocum
4,405,305 A 9/1983 Stephen
4,406,567 A 9/1983 Samis
4,425,119 A 1/1984 Berglund
4,445,896 A 5/1984 Gianturco
4,450,592 A 5/1984 Niederer
4,450,985 A 5/1984 Beard
4,456,011 A 6/1984 Warnecke
4,469,483 A 9/1984 Becker
4,494,545 A 1/1985 Slocum
4,506,676 A 3/1985 Duska
4,529,635 A 7/1985 Sheldon
4,543,088 A * 9/1985 Bootman .......... A61M 39/0208 604/288.02
4,549,879 A 10/1985 Groshong
4,559,043 A 12/1985 Whitehouse
4,559,046 A 12/1985 Groshong
4,560,375 A 12/1985 Schulte
4,571,749 A 2/1986 Fischell
4,576,595 A 3/1986 Aas
4,587,954 A 5/1986 Haber
4,612,877 A 9/1986 Hayes
4,626,244 A 12/1986 Reinicke
4,627,844 A 12/1986 Schmitt
4,634,427 A 1/1987 Hannula
4,636,194 A 1/1987 Schulte
4,636,213 A 1/1987 Pakiam
4,645,495 A 2/1987 Vaillancourt
4,653,508 A 3/1987 Cosman
4,655,765 A 4/1987 Swift
4,657,024 A 4/1987 Coneys
4,662,652 A 5/1987 Hargis
4,668,221 A 5/1987 Luther
4,671,796 A 6/1987 Groshong
4,673,394 A * 6/1987 Fenton, Jr. ........ A61M 39/0208 604/905
4,681,560 A 7/1987 Schulte
4,684,365 A 8/1987 Reinicke
4,685,447 A 8/1987 Iversen
4,685,905 A 8/1987 Jeanneret nee Aab
4,692,146 A 9/1987 Hilger
4,695,273 A 9/1987 Brown
4,697,595 A 10/1987 Breyer
4,701,166 A 10/1987 Groshong
4,704,103 A 11/1987 Herbert
4,710,167 A 12/1987 Lazorthes
4,710,174 A 12/1987 Moden
4,718,894 A 1/1988 Lazorthes
4,728,894 A 3/1988 Yoda
4,743,231 A 5/1988 Kay
4,753,640 A 6/1988 Nichols
4,755,173 A 7/1988 Konopka
4,760,837 A 8/1988 Petit
4,762,517 A 8/1988 Mcintyre
4,767,410 A 8/1988 Moden
4,772,270 A 9/1988 Wiita
4,772,276 A 9/1988 Wiita
4,773,552 A 9/1988 Boege
4,778,452 A 10/1988 Moden
4,781,680 A 11/1988 Redmond
4,781,685 A 11/1988 Lehmann
4,781,695 A 11/1988 Dalton
4,802,885 A 2/1989 Weeks
4,804,054 A 2/1989 Howson
4,820,273 A 4/1989 Reinicke
4,822,341 A 4/1989 Colone
4,840,615 A 6/1989 Hancock
4,848,346 A 7/1989 Crawford
4,857,053 A 8/1989 Dalton
4,861,341 A 8/1989 Woodburn
4,863,470 A 9/1989 Carter
4,886,501 A 12/1989 Johnston
4,892,518 A 1/1990 Cupp
4,904,241 A 2/1990 Bark
4,905,709 A 3/1990 Bieganski
4,909,250 A 3/1990 Smith
4,915,690 A 4/1990 Cone
4,928,298 A 5/1990 Tanaka
4,929,236 A 5/1990 Sampson
4,955,861 A 9/1990 Enegren
4,963,133 A 10/1990 Whipple
4,966,583 A 10/1990 Debbas
4,973,319 A 11/1990 Melsky
4,983,162 A 1/1991 Metais
4,995,108 A 2/1991 Tanaka
5,002,735 A 3/1991 Alberhasky
5,009,644 A 4/1991 Mcdonald
5,013,298 A 5/1991 Moden

(56) References Cited

U.S. PATENT DOCUMENTS 5,041,098 A 8/1991 Loiterman
5,044,955 A 9/1991 Jagmin
5,045,060 A 9/1991 Melsky
5,045,064 A 9/1991 Idriss
5,084,015 A 1/1992 Moriuchi
5,085,216 A 2/1992 Henley, Jr.
5,090,066 A 2/1992 Schoepe
5,092,849 A 3/1992 Sampson
5,108,317 A 4/1992 Beinhaur
5,108,377 A 4/1992 Cone
5,112,301 A 5/1992 Fenton, Jr.
5,112,303 A 5/1992 Pudenz
5,129,891 A 7/1992 Young
5,137,529 A 8/1992 Watson
5,147,483 A 9/1992 Melsky
5,152,753 A 10/1992 Laguette
5,156,600 A 10/1992 Young
5,158,547 A 10/1992 Doan
5,167,629 A 12/1992 Vertenstein
5,167,633 A 12/1992 Mann
5,167,638 A 12/1992 Felix
5,171,228 A 12/1992 Mcdonald
5,176,653 A 1/1993 Metals
5,176,662 A 1/1993 Bartholomew
5,178,612 A 1/1993 Fenton, Jr.
5,180,365 A 1/1993 Ensminger
5,185,003 A 2/1993 Brethauer
5,189,690 A 2/1993 Samuel
5,193,106 A 3/1993 DeSena
5,195,122 A 3/1993 Fabian
5,195,123 A 3/1993 Clement
5,199,948 A 4/1993 Mcphee
5,201,715 A 4/1993 Masters
5,203,771 A 4/1993 Melker
5,203,777 A 4/1993 Lee
5,207,644 A 5/1993 Strecker
5,213,574 A 5/1993 Tucker
5,215,537 A 6/1993 Lynn
5,222,499 A 6/1993 Allen
D337,637 S 7/1993 Tucker
5,224,938 A 7/1993 Fenton, Jr.
5,263,930 A 11/1993 Ensminger
D342,134 S 12/1993 Mongeon
5,281,199 A 1/1994 Ensminger
5,281,205 A 1/1994 Mcpherson
5,290,263 A 3/1994 Wigness
5,295,658 A 3/1994 Atkinson
5,299,253 A 3/1994 Wessels
5,309,863 A 5/1994 Leeb, Jr.
5,318,545 A 6/1994 Tucker
5,320,100 A 6/1994 Herweck
5,322,511 A 6/1994 Armbruster
5,328,480 A 7/1994 Melker
5,332,398 A 7/1994 Miller
5,334,153 A 8/1994 Mcintyre
5,336,194 A 8/1994 Polaschegg
5,338,398 A 8/1994 Szwejkowski
5,350,360 A 9/1994 Ensminger
5,352,204 A 10/1994 Ensminger
5,356,381 A 10/1994 Ensminger
5,360,407 A 11/1994 Leonard
5,383,233 A 1/1995 Russell
5,383,858 A 1/1995 Reilly
D355,240 S 2/1995 Gladfelter
5,387,192 A 2/1995 Glantz
5,394,457 A 2/1995 Leibinger
5,395,324 A 3/1995 Hinrichs
5,397,329 A 3/1995 Allen
5,399,168 A * 3/1995 Wadsworth, Jr. ........................... A61M 39/0208 604/539
5,405,402 A 4/1995 Dye
5,417,565 A 5/1995 Long
5,421,814 A 6/1995 Geary
5,423,334 A 6/1995 Jordan
5,425,762 A 6/1995 Muller
5,429,617 A 7/1995 Hammersmark
5,433,480 A 7/1995 Gresham
5,456,698 A 10/1995 Byland
5,476,460 A * 12/1995 Montalvo ......... A61M 39/0208 604/8
5,476,880 A 12/1995 Cooke
5,484,402 A 1/1996 Saravia
5,507,813 A 4/1996 Dowd
5,509,805 A 4/1996 Jagmin
5,513,637 A 5/1996 Twiss
5,514,103 A 5/1996 Srisathapat
5,520,632 A 5/1996 Leveen
5,527,307 A 6/1996 Srisathapat
5,562,617 A 10/1996 Finch, Jr.
5,562,618 A 10/1996 Cai
5,575,770 A 11/1996 Melsky
5,593,028 A 1/1997 Haber
5,607,393 A 3/1997 Ensminger
5,607,407 A 3/1997 Tolkoff
5,620,419 A 4/1997 Lui
5,637,102 A 6/1997 Tolkoff
5,638,832 A 6/1997 Singer
5,647,855 A 7/1997 Trooskin
5,662,600 A 9/1997 Watson
5,662,612 A 9/1997 Niehoff
5,676,146 A 10/1997 Scarborough
5,695,424 A 12/1997 Mizuta
5,695,490 A 12/1997 Flaherty
5,702,128 A 12/1997 Maxim
5,702,363 A 12/1997 Flaherty
5,704,915 A 1/1998 Melsky
5,709,668 A 1/1998 Wacks
5,713,844 A 2/1998 Peyman
5,713,858 A 2/1998 Heruth
5,718,382 A 2/1998 Jaeger
5,718,682 A 2/1998 Tucker
5,719,382 A 2/1998 White
5,725,507 A 3/1998 Petrick
5,733,336 A 3/1998 Neuenfeldt
5,733,400 A 3/1998 Gore
5,741,228 A 4/1998 Lambrecht
5,743,891 A 4/1998 Tolkoff
5,746,460 A 5/1998 Marohl
5,758,667 A 6/1998 Slettenmark
5,769,823 A 6/1998 Otto
5,773,552 A 6/1998 Hutchings
5,776,188 A 7/1998 Shepherd
5,792,104 A 8/1998 Speckman
5,792,116 A 8/1998 Berg
5,810,789 A 9/1998 Powers
5,824,071 A 10/1998 Nelson
5,830,172 A 11/1998 Leveen
5,833,654 A 11/1998 Powers
5,835,563 A 11/1998 Navab
5,836,935 A 11/1998 Ashton
5,843,069 A 12/1998 Butler
5,848,989 A 12/1998 Villani
5,868,702 A 2/1999 Stevens
5,882,353 A 3/1999 Vanbeek
5,895,424 A 4/1999 Steele, Sr.
5,906,596 A 5/1999 Tallarida
5,908,414 A 6/1999 Otto
5,916,263 A 6/1999 Goicoechea
5,919,160 A 7/1999 Sanfilippo, II
5,925,017 A 7/1999 Kriesel
5,925,030 A 7/1999 Gross
5,931,829 A 8/1999 Burbank
5,935,084 A 8/1999 Southworth
5,944,023 A 8/1999 Johnson
5,944,688 A 8/1999 Lois
5,944,712 A 8/1999 Frassica
5,947,953 A 9/1999 Ash
5,951,512 A * 9/1999 Dalton ............. A61M 39/0208 604/890.1
5,951,522 A 9/1999 Rosato
5,954,687 A 9/1999 Baudino
5,957,890 A 9/1999 Mann
5,968,011 A 10/1999 Larsen

(56) References Cited

U.S. PATENT DOCUMENTS 5,970,162 A 10/1999 Kawashima
5,989,216 A 11/1999 Johnson
5,989,239 A 11/1999 Finch
5,997,524 A 12/1999 Burbank
6,007,516 A 12/1999 Burbank
6,013,051 A 1/2000 Nelson
6,013,058 A 1/2000 Prosl
6,017,331 A 1/2000 Watts
6,022,335 A 2/2000 Ramadan
6,033,389 A 3/2000 Cornish
6,039,712 A 3/2000 Fogarty
6,077,756 A 6/2000 Lin
6,086,555 A 7/2000 Eliasen
6,090,066 A 7/2000 Schnell
6,102,884 A 8/2000 Squitieri
6,113,572 A 9/2000 Gailey
6,120,492 A 9/2000 Finch
6,161,033 A 12/2000 Kuhn
6,171,198 B1 1/2001 Lizama Troncoso
6,171,298 B1 1/2001 Matsuura
6,174,330 B1 1/2001 Stinson
6,190,352 B1 2/2001 Haarala
6,193,684 B1 2/2001 Burbank
6,198,807 B1 3/2001 DeSena
6,203,570 B1 3/2001 Baeke
6,213,973 B1 4/2001 Eliasen
6,251,059 B1 6/2001 Apple
D445,175 S 7/2001 Bertheas
6,269,148 B1 7/2001 Jessop
6,287,293 B1 9/2001 Jones
6,290,677 B1 9/2001 Arai
6,302,875 B1 10/2001 Makower
6,305,413 B1 10/2001 Fischer
D450,115 S 11/2001 Bertheas
6,332,874 B1 12/2001 Eliasen
6,347,241 B2 2/2002 Burbank
6,355,021 B1 3/2002 Nielsen
6,356,782 B1 3/2002 Sirimanne
6,361,557 B1 3/2002 Gittings
6,398,764 B1 6/2002 Finch, Jr.
6,419,680 B1 7/2002 Cosman
6,450,937 B1 9/2002 Mercereau
6,459,772 B1 10/2002 Wiedenhoefer
6,471,674 B1 10/2002 Emig
6,478,783 B1 11/2002 Moorehead
6,482,217 B1 11/2002 Pintor
6,494,867 B1 12/2002 Sten-Olof
6,497,062 B1 12/2002 Koopman
6,500,155 B2 12/2002 Sasso
6,503,228 B1 1/2003 Li
6,527,754 B1 3/2003 Tallarida
6,537,255 B1 3/2003 Raines
RE38,074 E 4/2003 Recinella
6,562,023 B1 5/2003 Marrs
6,582,418 B1 6/2003 Verbeek
6,613,002 B1 9/2003 Clark
6,613,662 B2 9/2003 Wark
D480,942 S 10/2003 Ishida
6,629,950 B1 10/2003 Levin
6,632,217 B2 10/2003 Harper
6,652,486 B2 11/2003 Bialecki
6,652,503 B1 11/2003 Bradley
6,676,633 B2 1/2004 Smith
6,697,664 B2 2/2004 Kienzle, III
6,705,316 B2 3/2004 Blythe
6,719,721 B1 4/2004 Okazaki
6,719,739 B2 4/2004 Verbeek
6,738,531 B1 5/2004 Funahashi
6,755,842 B2 6/2004 Kanner
6,758,841 B2 7/2004 Haarala
6,767,356 B2 7/2004 Kanner
6,784,783 B2 8/2004 Scoggin
D498,894 S 11/2004 Gould
6,826,257 B2 11/2004 Sayre
6,852,106 B2 2/2005 Watson
6,878,136 B2 4/2005 Fleury
6,878,137 B2 4/2005 Benchetrit
6,949,084 B2 9/2005 Marggi
6,962,580 B2 11/2005 Adams
6,971,390 B1 12/2005 Vasek
6,994,315 B2 2/2006 Ryan
6,997,914 B2 2/2006 Smith
7,008,377 B2 3/2006 Beane
7,008,412 B2 3/2006 Maginot
7,016,456 B2 3/2006 Basu
7,018,361 B2 3/2006 Gillespie, Jr.
D518,573 S 4/2006 French
7,044,942 B2 5/2006 Jolly
7,056,316 B1 6/2006 Burbank
7,070,591 B2 7/2006 Adams
7,072,704 B2 7/2006 Bucholz
7,074,232 B2 7/2006 Kanner
7,076,305 B2 7/2006 Imran
7,083,593 B2 8/2006 Stultz
7,108,686 B2 9/2006 Burke
7,123,690 B1 10/2006 Brown
7,131,962 B1 11/2006 Estabrook
7,140,769 B2 11/2006 Kay
7,186,236 B2 3/2007 Gibson
7,191,011 B2 3/2007 Cantlon
7,198,631 B2 4/2007 Kanner
7,214,207 B2 5/2007 Lynch
7,214,215 B2 5/2007 Heinzerling
7,223,257 B2 5/2007 Shubayev
7,229,417 B2 6/2007 Foerster
7,235,067 B2 6/2007 Morris
D546,440 S 7/2007 Burnside
7,242,982 B2 7/2007 Singhal
7,252,469 B2 8/2007 Zaluzec
7,252,649 B2 8/2007 Sherry
7,261,705 B2 8/2007 Edoga
D554,253 S 10/2007 Kornerup
7,275,682 B2 10/2007 Excoffier
7,276,075 B1 10/2007 Callas
D556,153 S 11/2007 Burnside
7,306,579 B2 12/2007 Fujii
7,311,702 B2 12/2007 Tallarida
7,318,816 B2 1/2008 Bobroff
7,318,818 B2 1/2008 Yashiro
7,322,953 B2 1/2008 Redinger
D562,443 S 2/2008 Zinn
7,331,130 B2 2/2008 Schweikert
7,331,948 B2 2/2008 Skarda
7,333,013 B2 2/2008 Berger
D564,449 S 3/2008 Dewberry
7,347,838 B2 3/2008 Kulli
7,351,233 B2 4/2008 Parks
7,377,915 B2 5/2008 Rasmussen
D574,950 S 8/2008 Zawacki
7,413,564 B2 8/2008 Morris
D578,203 S 10/2008 Bizup
7,445,614 B2 11/2008 Bunodiere
D582,032 S 12/2008 Bizup
7,465,847 B2 12/2008 Fabian
D595,892 S 7/2009 Smith
7,563,025 B2 7/2009 Kay
7,651,483 B2 1/2010 Byrum
D612,479 S 3/2010 Zawacki
7,785,302 B2 8/2010 Powers
7,833,281 B2 11/2010 Lehman
8,025,639 B2 9/2011 Powers
8,257,325 B2 * 9/2012 Schweikert ........... A61M 5/007
604/288.04
10,179,230 B2 1/2019 Powers
2001/0051766 A1 12/2001 Gazdzinski
2001/0056266 A1 12/2001 Tallarida
2002/0082610 A1 6/2002 Cioanta
2002/0095205 A1 7/2002 Edwin
2002/0173769 A1 11/2002 Gray
2003/0010929 A1 1/2003 Priewe
2003/0028173 A1 2/2003 Forsberg
2003/0032918 A1 2/2003 Quinn
2003/0060842 A1 3/2003 Chin
2003/0139812 A1 7/2003 Garcia

(56) References Cited

U.S. PATENT DOCUMENTS

| | | | | |
|---|---|---|---|---|
| 2003/0191452 | A1 | 10/2003 | Meglin | |
| 2004/0002693 | A1 | 1/2004 | Bright | |
| 2004/0006316 | A1 | 1/2004 | Patton | |
| 2004/0019356 | A1 | 1/2004 | Fraser | |
| 2004/0020462 | A1 | 2/2004 | Sauler | |
| 2004/0044306 | A1 | 3/2004 | Lynch | |
| 2004/0056266 | A1 | 3/2004 | Suh | |
| 2004/0064110 | A1 | 4/2004 | Forsell | |
| 2004/0093069 | A1 | 5/2004 | Priewe | |
| 2004/0106878 | A1 | 6/2004 | Skujins | |
| 2004/0106891 | A1 | 6/2004 | Langan | |
| 2004/0157952 | A1 | 8/2004 | Soffiati | |
| 2004/0158207 | A1 | 8/2004 | Hunn | |
| 2004/0167543 | A1 | 8/2004 | Mazzocchi | |
| 2004/0181186 | A1 | 9/2004 | Gellman | |
| 2004/0199129 | A1 | 10/2004 | DiMatteo | |
| 2004/0204692 | A1 | 10/2004 | Eliasen | |
| 2004/0204962 | A1 | 10/2004 | Howser | |
| 2004/0225254 | A1 | 11/2004 | Tanaka | |
| 2004/0254536 | A1 | 12/2004 | Conlon | |
| 2004/0254537 | A1 | 12/2004 | Conlon | |
| 2005/0038390 | A1 | 2/2005 | Fago | |
| 2005/0049553 | A1 | 3/2005 | Triplett | |
| 2005/0070875 | A1 | 3/2005 | Kulessa | |
| 2005/0077688 | A1 | 4/2005 | Voegele | |
| 2005/0085723 | A1 | 4/2005 | Huebner | |
| 2005/0113806 | A1 | 5/2005 | De Carvalho | |
| 2005/0131352 | A1 | 6/2005 | Conlon | |
| 2005/0148866 | A1 | 7/2005 | Gunderson | |
| 2005/0148956 | A1 | 7/2005 | Conlon | |
| 2005/0148957 | A1 | 7/2005 | Girard | |
| 2005/0159717 | A1 | 7/2005 | Holtermann | |
| 2005/0171502 | A1 | 8/2005 | Daly | |
| 2005/0182857 | A1 | 8/2005 | Kong | |
| 2005/0209573 | A1 | 9/2005 | Brugger | |
| 2005/0215874 | A1 | 9/2005 | Wang | |
| 2005/0215876 | A1 | 9/2005 | Chen | |
| 2005/0241203 | A1 | 11/2005 | Lizotte | |
| 2005/0277899 | A1 | 12/2005 | Conlon | |
| 2005/0283119 | A1 | 12/2005 | Uth | |
| 2006/0009788 | A1 | 1/2006 | Freeman | |
| 2006/0017341 | A1 | 1/2006 | Hahn | |
| 2006/0084929 | A1 | 4/2006 | Eliasen | |
| 2006/0089619 | A1 | 4/2006 | Ginggen | |
| 2006/0100592 | A1 | 5/2006 | Eliasen | |
| 2006/0116648 | A1 | 6/2006 | Hamatake | |
| 2006/0173410 | A1 | 8/2006 | Moberg | |
| 2006/0173424 | A1 | 8/2006 | Conlon | |
| 2006/0178647 | A1* | 8/2006 | Stats | A61M 39/0208 604/288.01 |
| 2006/0184142 | A1 | 8/2006 | Schon | |
| 2006/0217359 | A1 | 9/2006 | Wentworth | |
| 2006/0217668 | A1 | 9/2006 | Schulze | |
| 2006/0224128 | A1 | 10/2006 | Lurvey | |
| 2006/0224129 | A1 | 10/2006 | Beasley | |
| 2006/0247584 | A1* | 11/2006 | Sheetz | A61B 6/032 604/288.02 |
| 2006/0253076 | A1 | 11/2006 | Butts | |
| 2007/0007839 | A1 | 1/2007 | Lin | |
| 2007/0014921 | A1 | 1/2007 | Kimball | |
| 2007/0055290 | A1 | 3/2007 | Lober | |
| 2007/0073250 | A1 | 3/2007 | Schneiter | |
| 2007/0078391 | A1 | 4/2007 | Wortley | |
| 2007/0078416 | A1 | 4/2007 | Eliasen | |
| 2007/0078432 | A1 | 4/2007 | Halseth | |
| 2007/0083156 | A1 | 4/2007 | Muto | |
| 2007/0149920 | A1 | 6/2007 | Michels | |
| 2007/0149921 | A1 | 6/2007 | Michels | |
| 2007/0149947 | A1 | 6/2007 | Byrum | |
| 2007/0161958 | A1 | 7/2007 | Glenn | |
| 2007/0161985 | A1 | 7/2007 | Demakas | |
| 2007/0179456 | A1 | 8/2007 | Glenn | |
| 2007/0185462 | A1 | 8/2007 | Byrum | |
| 2007/0191773 | A1 | 8/2007 | Wojcik | |
| 2007/0208313 | A1 | 9/2007 | Conlon | |
| 2007/0219510 | A1 | 9/2007 | Zinn | |
| 2007/0233017 | A1 | 10/2007 | Zinn | |
| 2007/0233018 | A1 | 10/2007 | Bizup | |
| 2007/0248256 | A1 | 10/2007 | Fabian | |
| 2007/0255226 | A1 | 11/2007 | Tennican | |
| 2007/0255234 | A1 | 11/2007 | Haase | |
| 2007/0270691 | A1 | 11/2007 | Bailey | |
| 2007/0270770 | A1 | 11/2007 | Bizup | |
| 2007/0276344 | A1 | 11/2007 | Bizup | |
| 2007/0299408 | A1 | 12/2007 | Alferness | |
| 2008/0004642 | A1 | 1/2008 | Birk | |
| 2008/0008654 | A1 | 1/2008 | Clarke | |
| 2008/0027411 | A1 | 1/2008 | Von Oepen | |
| 2008/0039820 | A1 | 2/2008 | Sommers | |
| 2008/0108949 | A1 | 5/2008 | Beasley | |
| 2008/0114308 | A1 | 5/2008 | Di Palma | |
| 2008/0138387 | A1 | 6/2008 | Machiraju | |
| 2008/0208236 | A1 | 8/2008 | Hobbs | |
| 2008/0281279 | A1 | 11/2008 | Hoendervoogt | |
| 2008/0319398 | A1 | 12/2008 | Bizup | |
| 2009/0035582 | A1 | 2/2009 | Nakatani | |
| 2009/0171436 | A1 | 7/2009 | Casanova | |
| 2009/0199857 | A1 | 8/2009 | Peake | |
| 2009/0204072 | A1 | 8/2009 | Amin | |
| 2009/0227862 | A1 | 9/2009 | Smith | |
| 2010/0042073 | A1 | 2/2010 | Oster | |
| 2010/0069743 | A1 | 3/2010 | Sheetz | |
| 2011/0054312 | A1 | 3/2011 | Bell | |
| 2019/0252603 | A1 | 8/2019 | Wiley | |
| 2019/0275311 | A1 | 9/2019 | Hibdon | |

FOREIGN PATENT DOCUMENTS

| | | | |
|---|---|---|---|
| DE | 19745654 | A1 | 4/1999 |
| EP | 0750520 | | 1/1997 |
| EP | 0750520 | B1 | 8/2000 |
| EP | 1238662 | A2 | 9/2002 |
| EP | 1238682 | | 9/2002 |
| FR | 1509165 | A | 1/1968 |
| FR | 2569987 | A1 | 6/1969 |
| FR | 2569987 | | 3/1986 |
| FR | 2586569 | A1 | 3/1987 |
| GB | 2203342 | A | 10/1988 |
| JP | S6338535 | | 3/1988 |
| JP | 2500388 | Y2 | 6/1996 |
| JP | H08168322 | A | 7/1996 |
| JP | 2602109 | B2 | 4/1997 |
| JP | 2602109 | | 12/1999 |
| JP | 2003102831 | A | 4/2003 |
| JP | 2004350937 | A | 12/2004 |
| JP | 2005103284 | | 4/2005 |
| JP | 2006025948 | A | 2/2006 |
| JP | 2008168322 | A | 7/2008 |
| WO | 8600213 | A1 | 1/1986 |
| WO | 9305730 | A1 | 4/1993 |
| WO | 9514504 | A1 | 6/1995 |
| WO | 0004800 | A1 | 2/2000 |
| WO | 0011726 | A1 | 3/2000 |
| WO | 0014504 | A1 | 3/2000 |
| WO | 0017337 | A1 | 3/2000 |
| WO | 0047264 | A1 | 8/2000 |
| WO | 0047548 | A1 | 8/2000 |
| WO | 0047549 | | 8/2000 |
| WO | 0100480 | A1 | 1/2001 |
| WO | 0247549 | A1 | 6/2002 |
| WO | 02100480 | A2 | 12/2002 |
| WO | 03037215 | A2 | 5/2003 |
| WO | 03086508 | A1 | 10/2003 |
| WO | 2004071555 | A2 | 8/2004 |
| WO | 2005037055 | A2 | 4/2005 |
| WO | 2006079905 | | 8/2006 |
| WO | 2006130133 | A1 | 12/2006 |
| WO | 2006134100 | A1 | 12/2006 |
| WO | 2007025266 | | 3/2007 |
| WO | 2007092210 | A1 | 8/2007 |
| WO | 2007094898 | A2 | 8/2007 |
| WO | 2007098771 | A2 | 9/2007 |
| WO | 2007126645 | A2 | 11/2007 |

(56) References Cited

FOREIGN PATENT DOCUMENTS

| | | | |
|---|---|---|---|
| WO | 2008019236 | A1 | 2/2008 |
| WO | 2008147760 | A1 | 12/2008 |
| WO | 2008147760 | A2 | 12/2008 |

OTHER PUBLICATIONS

International Application No. PCT/US2008/010520, International Search Report, dated Feb. 24, 2009, 2 pages.
International Application No. PCT/US2008/078976, International Search Report and Written Opinion, dated Apr. 3, 2009, 6 pages.
International Application No. PCT/US2009/062854, International Search Report, dated Dec. 23, 2009,2 pages.
International Application No. POTYUS2008/010520, Written Opinion, dated Feb. 24, 2009,4 pages.
International Preliminary Report on Patentability and Written Opinion received for PCT Patent Application No. PCT/US2006/015695, dated on Oct. 30, 2007,9 pages.
International Preliminary Report on Patentability and Written Opinion Received for PCT Patent Application No. PCT/US2006/016056, dated on Oct. 30, 2007, 9 pages.
International Preliminary Report on Patentability and Written Opinion Received for PCT Patent Application No. PCT7US2006/049007, dated on Jul. 1, 2008, 5 pages.
International Preliminary Report on Patentability and Written Opinion Received for PCT Patent Application No. PCT/ | JS2006/008022 , dated on Sep. 12, 2007, 6 pages.
International Preliminary Report on Patentability dated Jan. 2, 2009; PCT/US07/06776 (6 pages).
International Preliminary Report on Patentability Received for PCT Application No. PCT/US2007/011015, Nov. 23, 2009, 9 pages.
International Preliminary Report on Patentability Received for PCT Application No. PCT/US2008/070330. 9 pages.
International Preliminary Report on Patentability received for PCT Patent Application No. PCT/US2007/006776 , dated Mar. 6, 2008, 3 pages.
International Preliminary Report on Patentability received for PCT Patent Application No. PCT/US2007/006776, completed on Nov. 16, 2008, 3 pages.
International Search Report and Written Opinion received for International Patent Application No. PCT/US2012/050586, dated Oct. 22, 2012.
International Search Report and Written Opinion received for PCT Patent Application No. PCT/US2007/006776, dated on Dec. 18, 2007, 3 pages.
International Search Report and Written Opinion Received for PCT Patent Application No. PCT/US2008/067679, Sep. 30, 2008, 7 pages.
International Search Report and Written Opinion Received for PCT Patent Application No. PCT/US06/49007, Oct. 1, 2007,6 pages.
International Search Report and Written Opinion Received for PCT Patent Application No. PCT/US08/070345, Dec. 1, 2008, 11 pages.
International Search Report and Written Opinion Received for PCT Patent Application No. PCT/US2006/015695, Jan. 11, 2007, 8 pages.
International Search Report and Written Opinion Received for PCT Patent Application No. PCT/US2007/011015, Jun. 10, 2008, 5 pages.
International Search Report and Written Opinion Received for PCT Patent Application No. PCT/US2007/011456, Aug. 28, 2008, 6 pages.
International Search Report and Written Opinion Received for PCT Patent Application No. PCT/US2008/010520, Feb. 24, 2009, 6 pages.
International Search Report and Written Opinion Received for PCT Patent Application No. PCT/US2008/070330, dated Dec. 1, 2008, 10 pages.
International Search Report and Written Opinion received for PCT Patent Application No. PCT/US2007/006776, Dated an Jan. 2, 2009, 6 pages.
International Search Report Received for PCT Patent Application No. PCT/US1999/028695. Apr. 11, 2000, 2 pages.
International Search Report Received for PCT Patent Application No. PCT/US06/008022, mailed on Jul. 5, 2006, 2 Pages.
International Search Report Received for PCT Patent Application No. PCT/US2009/062854, dated on Dec. 23, 2009, 2 pages.
IsoMed Constant-Flow Infusion System (Year: 2000), 111 pages.
Johnson, Kathleen A., "Power Injectable Portal Systems," Journal of Radiology Nursing, vol. 28, Issue 1, Mar. 2009, 6 pages.
JP 2010-513443, Office Action, dated Nov. 8, 2012, 4 pages.
Lamaitre Vascular, Port Implantations: using the OptiLock Implantable Port, product information, available at <http://www.lemaitre.com/specs_pop.asp>, Apr. 2003, 14 pages.
LAP-BAND System Fact Sheet, 2007 Allergan, Inc., 2 pages.
LAP-BAND AP "System with Adjustable Gastric Banding system with OMNIFORM Design," Product Brochure, Jul. 2007, 16 pages.
LAP-BAND, Adjustable Gastric Banding System, BioEnlerics Corporation, Product Brochure, 12 pages.
Machine Translation of JP2004/350937A. Acquired on Feb. 15, 2018.
McKillop et al., "Retained Surgical Swab Misinterpreted as Epicardial Pacing Wire on Chest X Ray", 1996, Heart, f5:342.
Medcomp, PortCT Technology, Display at SIR Conference. Toronto, Canada, Mar. 2006, 1 page.
Medtronic IsoMed Constant Flow Infusion System (2000).
Notice of Opposition filed for European Patent Application No. 07753408.9 on Jul. 4, 2018, 24 pages.
Notice of Opposition filed for European Patent Application No. 08771600.7 on Jul. 25, 2018, 26 pages.
Notice of Opposition filed for European Patent Application No. 08781983.5 on Jul. 4, 2018,25 pages.
Nucleus Cochlear Implant Systems; User Manual for the ESPrit 3G speech processor and accessories, available at http://www.cochlearamericas.com/PDFs/UserManualSprint.pdf, Issue 2, Dec. 2001, 2 pages.
O'Connor et al., "Imaging of Retained Surgical Sponges in the Abdomen and Pelvis", 2003, AJR, 180:481-489.
Patent Assignment recorded for U.S. Appl. No. 12/143,377, on Aug. 4, 2008, 6 pages. (E4 Opposition / EP 2164559).
PCT Application No. US/2007/011015, International Search Report, dated Jun. 10, 2008, 1 page.
PCT Request Form as made available—on WIPO's Patentscope for PCT/US2007/06776.
PCT Request received for PCT Application No. PCT/US2008/67679, filed on Dec. 24, 2008,4 pages. (E3 Opposition / EP 2164559).
PCT/US06/49007 International Search Report, mailed Oct. 1, 2007, 2 pages.
PCT/US06/49007 Written Opinion, mailed Oct. 1, 2007, 4 pages.
PCT/US08/067657, International Search Report dated Sep. 19, 2008, 3 pages.
PCT/US08/067657, Written Opinion dated Sep. 19, 2008, 5 pages.
PCT/US08/067679 Written Opinion, mailed Sep. 30, 2008, 4 pages.
PCT/US08/070330 Written Opinion, mailed Dec. 1, 2008, 5 pages.
PCT/US08/070345 Written Opinion, mailed Dec. 1, 2008, 6 pages.
PCT/US08/67657, International Preliminary Report on Patentability, dated Nov. 2, 2009, 7 pages.
Plinski et ai., Implantable Cardioverter-Defribillators: Implications for the Nonelectrophysiologist, Annals of Internal medicine, Abstract of vol. 122, No. 10, pp. 770-777.
Port-A-Cath "Many PORT-A-CATH System Choices," Product Brochure, 1996 SIMS Deltec, Inc., 5 pages.
Port-A-Cath "Single-lumen Implantable Vascular Access Systems," Product Specifications, 2004 Smith Medical, 4 pages.
Port-A-Cath , Implantable Epidural, Aterial and Peritonial Access Systems, Internet Product Listing of Nov. 19, 2000, available at <http://web. archive.org/web/20001119035900/www.deltec.com/cPacspl.htm,>, Oct. 17, 2009,2 pages.
Port-A-Cath P.A.S. PORT Systems by Dcltec, Product Specifications, 1999, 2 pages.

(56) References Cited

OTHER PUBLICATIONS

PowerPort Guidelines for CT Technologists, Feel the New Standard of Care, 1 page. (D5 Opposition / EP 2081634).
U.S. Appl. No. 60/936,491, filed Jun. 20, 2007, 28 pages. (E2 Opposition / EP 2164559).
Rappolt, Richard T., et al., "Radiopaque Codification and X-ray identification of Ingested Drugs," Ingestive Radioiogy, May-Jun. 1966. 4 pages.
Reminders form FDA Regarding Ruptured Vascular Access Devices from Power Injection, Jul. 2004, 2 pages.
Salis et al., "Maximal Flow Rates Possible during Power Injection through Currently Available PICCs: An In-Vitro 3tudy", Journal of the Association for Vascular Access, vol. 15, No. 3, Mar. 2004, pp. 275-281.
Sandstede, Joern, "Pediatric CT," available online at www.multislice-ct.com, MultiSLICE-CT.com, version 02, May 2, 2003, 36 pages.
Sanelli, et al., "Safety and Feasibility of Using a Central Venous Catheter for Rapid Contrast Injection Rates." American Journal of Radiology, vol. 183, pp. 1829-1834, Dec. 2004, 6 pages.
Sawyer, "Do It by Design: An Introduction to Human Factors in Medical Devices", U.S. Department of Health and Human Services, Public Health Service, Food and Drug Administration, Center for Devices and Radiological Health, Dec. 1996, 55 pages.
Shah Tilak M., Radiopaque Polymer Formulations for Medical Devices, Medical Device and Diagnostic Industry, Mar. 2000, 6 pages.
Signs, Symbols, and Icons: Pre-history to the Computer Age, author: Rosemary Sassoon and Albertine Gaur, first published in 1997, 3 pages.
Smith, Lisa Hartkoph, "Implanted Ports, Computer Tomography, Power Injectors, and Catheter Rupture." Clinical Journal of Oncology Nursing, vol. 12, No. Oct. 5, 2008, 4 pages.
Solomon et al., CIN Strategies: Anticipate, Manage, Prevent, Supplement to Imaging Economics, May 1, 2007, 20 Pages.
Steinbach et al., Breast Implants, Common Complications, and Concurrent Breast Disease, RadioGraphtes. vol. 13, No. 1, Jan. 1, 1993, pp. 95-118.
Stevens et al., "A Randomized, Prospective Trial of Conventional Vascular Poits vs. The Voitex "Clear-Flow" Reservoir Port in Adult Oncology Patients", The Journal of Vascular Access Devices, 2000, pp. 37-40.
Sullivan et al. "Radiopaque Markers on Mammary Implants." American Journal of Roentgenology 153(2):428, Aug. 1989, 2 pages.
Teichgraber et al., Central Venous Access Catheters: Radiological Management of Complications, Cardiovascular and Interventional Radiology, Review Article, Jul. 31, 2003, 13 pages.
The extended European search report, dated Mar. 3, 2018, for EP App. No. 17193828.5, which claims priority to U.S. Appl. No. 60/961,133, filed Jul. 19, 2007, 8 pages.
Thistlethwaitf et al., Generalized Feature-Based RSA of Orthopedic Implants, Summer Bioengineering Conference Sonesta Beach Resort in Key Biscayne, Florida, Jun. 25-29, 2 pages.
Title User Manual Sprint. Available at http://www. cochlearamericas com/PDFs/UserManuaiSpnnt.pdf, Dec. 01. 2.012,2 Pages.
Transmittal letter and cover sheet for U.S. Appl. No. 60/658,518, filed Mar. 4, 2005, 2 Pages. (E3 Opposition / EP 2081634).
U U.S. Appl. No. 60/852,591, filed Oct. 18, 2006,23 pages. (E2 Opposition / EP 2081634).
U.S. Appl. No. 10/374,000, Response to Office Action, filed Sep. 21, 2009, 13 pages.
U.S. Appl. No. 11/725,287, Declaration of Interference, mailed Nov. 10, 2011, 6 pages.
U.S. Appl. No. 11/725,287, Notice of Allowance, dated Aug. 29, 2009, 4 pages.
U.S. Appl. No. 11/725,287, Notice of Withdrawal from Issue, dated Oct. 23, 2009, 1 page.
U.S. Appl. No. 11/725,287, Office Action, dated Dec. 7, 2011, 4 pages.
U.S. Appl. No. 11/725,287, Office Action, dated Mar. 29, 2010.
U.S. Appl. No. 11/725,287, Office Action, mailed Dec. 3, 2008, 7 pages.
U.S. Appl. No. 11/725,287, Office Action, mailed Jun. 12, 20095 pages.
U.S. Appl. No. 11/725,287, Office Action, mailed Oct. 5, 2011, 6 pages.
U.S. Appl. No. 11/725,287, Response, filed Feb. 24, 2009, 9 pages.
U.S. Appl. No. 11/725,287, Response, filed Jan. 6, 2011, 10 pages.
U.S. Appl. No. 11/725,287, Response, filed Jul. 28, 2009, 4 pages.
U.S. Appl. No. 11/725,287, Response, filed Sep. 29, 2010, 10 pages.
U.S. Appl. No. 11/725,287, Response, mailed Oct. 11, 20115 pages.
U.S. Appl. No. 11/725,287, Supplemental Response and Suggestion of Interference, filed Feb. 18, 2011, 64 pages.
U.S. Appl. No. 11/725,287, Supplemental Response and Suggestion of Interference, filed May 26, 2011, 62 pages.
U.S. Appl. No. 12/175,182, Notice of Allowability, mailed Mar. 9, 2011, 5 pages.
U.S. Appl. No. 12/175,270, Office Action, dated Mar. 14, 2012 7 pages.
U.S. Appl. No. 12/420,007, Office Action, dated Feb. 18, 2010, 9 pages.
U.S. Appl. No. 12/420,007, Office Action, dated Jul. 14, 2009, 7 pages.
U.S. Food and Drug Administration, "Guidance for Institutional Review Boards and Clinical Investigators 1998 Update: Medical Devices." Version Sep. 10, 2008, 13 pages.
U.S. Appl. No. 29/247,954, Notice of Allowability, dated Jul. 30, 2007, 3 pages.
U.S. Appl. No. 29/247,954, Office Action, dated Apr. 6, 2007, 6 pages.
U.S. Appl. No. 29/284,454, filed Sep. 7, 2007, entitled "Implantable Port Device," issued Aug. 12. 2008 as U.S. Pat. No. D. 574,950, 8 pages.
U.S. Appl. No. 29/284,456, filed Sep. 7, 2007 entitled "Implantable Port Device," 8 pages.
U.S. Appl. No. 60/658,518 [64 pages].
U.S. Appl. No. 60/658,518, filed Mar. 4, 2005, 62 pages. (D1 Opposition / EP 2081634).
U.S. Appl. No. 60/675,309, filed Apr. 27, 2005, 100 pages.
U.S. Appl. No. 60/961,133, filed Jul. 19, 2007,24 pages. (E2 Opposition / EP 2180915).
Urquiola et al., Using Lead Foil as a Radiopaque Marker for Computerized Tomography Imaging When Implant Treatment Planning, The Journal of Prosthetic Dentistry, vol. 77, No. 2, 1997, pp. 227-228.
Vergara, et al., "Adverse Reactions to Contrast Media in CT: Effects of Temperature and lonic Property." Radiology, vol. 199, No. 2, May 1996, 4 pages.
Vogelzang Robertl, "Power Injection Through Central Venous Catheters: Physiological and Hemodynamic Considerations", The McGaw Medical Center of Northwestern University, Feinberg School of Medicine, 3 pages.
Walter et al., "Radiographic Identification of Commonly Used Implanted Pacemakers", The New England Journal of Medicine, 1969, vol. 281, 22:1230-1231.
Walter, "Radiographic Identification of Commonly Used Pulse Generators-1970", 1971, JAMA, vol. 215, 12: 1974-1975.
Weils S, Venous Access in Oncology and Haematology Patients: Part One, Nursing Standard, vol. 22, No. 52, pp. 39-46,. Sep. 3, 2008,9 pages.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001, 6 pages.
Wolfson et al., "Imaging of Surgical Paraphernalia: What Belongs in the Patient and What Does Not", 2000, Radiographics, 20:1665-1673.
"Extravasation of Radiologic Contrast." PA-PSRS Patient Safety Advisory—vol. 1, No. 3, Sep. 2004, 6 pages.
"Radiopaque Imprinting Enables Alternative to Angioplasty", Medical Product Manufacturing News, Apr. 2003,1 page.

(56) References Cited

OTHER PUBLICATIONS 9.75/1 0.0 em LAP-BAND System vs. 11 em LAP BAND System: For Product Manufactured Prior to Jul. 2001, LAP Band System Access Port Fill Guide 1 BioEnterics Corporation, Jul. 1, 2001, 1 page.
Bard Access System product drawings representative of the Bard Access System products on the market on or around Mar. 1995 as indicated by the Bard Access Systems Mar. 21, 1995 Product Release to Market form for "M.R.I. Port with 8 Fr. ChronoFlex Catheter," "M.R.I. Port with 8 Fr. ChronoFlex Catheter with Intro-Eze1M," "M.R.I. Port with 8 Fr. Chrono-Flex Catheter and Peel Apart." "M.R.I. Port with 8 Fr. ChronoFlex Catheter Demo Kit," 6 pages.
Bard Access Systems, "Power Ports", Brochure, (20070200), XP055501208.
Bard Access Systems, "PowerPort", Guidelines for CT Technologists, (20070200), XP055501207.
Bard Access Systems, Inc., "Hickman Subcutaneous Ports & Hickman/Broviac Catheters", Bard Exhibit, vol. 1017, Jan. 1, 1992.
Bard Access Systems, Inc., "Ports-Setting the Standard with a Comprehensive Family of Ports", Bard Exhibit vol. 1002, Jan. 1, 2003, pp. 1-17.
Bard Access Systems, Inc., "Power Port-Implantable Port-Feel the New Standard of Care-Guidelines for CT Technologists", Bard Exhibit 1004, C.R. Bard, Inc., Feb. 1, 2007, 1 Page.
Biffi et al., A Randomized, Prospective Trial of Central Venous Ports Connected to Standard Open-Ended or Groshong Catheters in Adult Oncology Patients, American Cancer Society vol. 92, No. 5, Sep. 1, 2001, pp. 1204-1212.
Biffi et al.. Use of Totally Implantable Central Venous Access Ports for High Dose Chemotherapy and Peripheral Blood Stem Cell Transplantation: Results of a Monocentre Series of 376 Patients, Annals of Oncology vol. 5, Jan. 11, 2004, pp. 296-300.
Biffi, R. Ct al. "Best Choice of Central Venous Insertion Site for the Prevention of Catheter-Related Complications in Adult Patients Who Need Cancer Therapy: A Randomized Trial." Annals of Oncology, Jan. 29, 2009, 6 pages.
Biffi, R. et al. "Use of totally implantable central venous access ports for high-dose chemotherapy and peripheral blood stem cell transplantation: results of a monocentro scries of 376 patients." Annals of Oncology 15:296-300, 2004, 5 pages.
BioEnterics LAP-BAND "Adjustable Gastric Banding System" by Inamed Health, Product Brochure, Dec. 2003, 22 pages.
Boswell Declaration for U.S. Pat. No. 8,257,325, issued on Sep. 4, 2012,8 pages. E6 Opposition / EP 2081634).
Brochure for PowerPort, Feel the New Standard of Care, 4 pages. (D6 Opposition / EP 2081634).
Carlson et al., "Safety Considerations in the Power Injection of Contrast Media via Central Venous Catheters During Computed Tomographic Examinations", Investigative Radiology, vol. 27, No. 5, May 1992, pp. 337-340.
CN Application No. 200880021187.6, Office Action dated Jul. 26, 2011, 5 pages with 6-page translation.
CN Application No. 200880021187.6, Reply dated Dec. 12, 2011, 6 pages.
Cope et al., Access Device Guidelines—Recommendations for Nursing Practice and Education, 2d Edition, 2004, 85 pages.
Costa, Nancy, "More Than Skin Deep: An Overview of Iodinated Contrast Media." Journal for the Association for Vascular Access, vol. 8, No. 4, 2003, 6 pages.
Costa, Nancy, "Understanding Contrast Media." Journal of Infusion Nursing, vol. 27, No., 5, Sep./Oct. 2004, 11 pages.
Coyle et al., "Power Injection of Contrast Media via Peripherally Inserted Central Catheters for CT", The Journal of the Association for Vascular Access (JAVA), vol. 15, No. 8, Aug. 2004, pp. 809-814.
Declaration of Kelly Christian, Director of Product Development at BARD Access Systems, Inc, in Support of and Depicting a Product on the Market by Quinto Company Approximately Ten Years Prior to Oct. 22, 2009, 1 page.
EP Application No. 07 794 615.0-2320, Extended European Search Report, dated Aug. 30, 2012, 6 pages.
EP Application No. 08 771 585.0-1526, Communication, dated Jun. 4, 2012, 6 pages.
EP Application No. 08 771 585.0, Communication, dated Dec. 28, 2011, 6 pages.
EP Application No. 08 771 585.0, Reply, dated Nov. 25, 2010,10 pages.
European Patent Office Communication, dated Dec. 15, 2005, for Application No. 99 964 086.5-1257, Applicant STD Manufacturing, Inc., 9 pages.
European Patent Office Communication, dated Mar. 1, 2005, for EP Application No. 99 964 086,5-1257, Applicant STD Manufacturing, Inc., 4 pages.
European Patent Office Communication, dated Mar. 30, 2005, for Application No. 99 964 086.5-1257, Applicant STD Manufacturing, Inc., 3 pages.
European Patent Office Communication, dated Sep. 2, 2008, for Application No. 06 751 411.7-1526, Applicant C.R. Bard, Inc., 4 pages.
Extended European Search Report received for EP Application No. EP 08781983.5, 5 pages.
Extended European Search Report Received for European Patent Application No 07753408.9, mailed on Aug. 24, 2012.
Extended European Search Report received for European Patent Application No. 17189436.3, mailed on Oct. 13, 2017.
Extreme Access, Bard Access Systems, Inc., Product Brochure, 2003, 5 pages.
Fallscheer, et al., "Injury to the Upper Extremity Caused by Extravasation of Contrast Medium: A True Emergency." Scandinavian Journal of Plastic and Reconstructive Surgery and Hand Surgery, vol. 41, pp. 26-32, 2007, 7 pages.
Funaki, "Central Venous Access: A Primer for the Diagnostic Radiologist", 2002, AJR, 179:309-318.
Gebauer et al., "Contrast Media Power Injection Using Central-Venous Port Catheters—Results of an In Vitro Study", Experimental Radiology, 2005, 177:1417-1423.
Guidance for Industry and FDA Staff, Use of Symbols on Labels and in Labeling of In Vitro Diagnostic Devices | Intended for Professional Use, Nov. 30, 2004, 12 pages.
Guidance on Medical Device Patient Labeling; Final Guidance for Industry and FDA Reviewers, Apr. 19, 2001, 54 rages.
Herts et al., "Power Injection of Contrast Media Using Central Venous Catheters: Feasibility, Safety and Efficacy", AJR.176(2), Feb. 2001, pp. 447-453.
Herts et al., Power Injection of Intravenous Contrast Material Through Central Venous Catheters for CT: In Vitro Evaluation, Radiology, vol. 200, No. 3, Sep. 1996, pp. 731-735.
Hou et al., Comparisons of Outcomes and Survivals for Two Central Venous Access Port Systems, Journal of surgical Oncology, vol. 91, Jan. 1, 2005, pp. 61-66.
Interference Decision for Patent Interference No. 105,860, declared on Nov. 10, 2011, 9 pages. (E5 Opposition / EP 2081634).
Interference Decision, Zinn vs Powers, Patent Interference No. 105,860, Paper 50, Sep. 11, 2012, 9 pages.
International Application No. PCT/TJS2006/016056, International Search Report, dated Sep. 20, 2006,4 pages.
International Application No. PCT/US1999/028695, International Preliminary Examination Report, dated Apr. 21, 2001, 4 pages.
International Application No. PCT/US1999/028695, International Search Report, dated Apr. 11, 2000, 2 pages.
International Application No. PCT/US2006/015695, Written Opinion, dated Oct. 30, 2007, 8 pages.
U.S. Appl. No. 12/175,270, Office Action, dated May 26, 2011, 6 pages.
U.S. Appl. No. 12/175,270, Office Action, dated Sep. 14, 2011, 6 pages.
U.S. Appl. No. 12/175,270, Response, filed Apr. 5, 2011, 7 pages.
U.S. Appl. No. 12/175,270, Response, filed Aug. 22, 2011, 18 pages.
U.S. Appl. No. 12/175,270, Response, filed Jan. 17, 2012, 10 pages.
U.S. Appl. No. 12/143,377, Office Action, mailed Apr. 27, 2009, 6 pages.

(56) References Cited

OTHER PUBLICATIONS

U.S. Appl. No. 11/368,954, Office Action, mailed Jan. 27, 2010, 7 pages.
U.S. Appl. No. 10/374,000, Advisory Action, mailed Jan. 23, 2007, 3 pages.
U.S. Appl. No. 10/374,000, Office Action, mailed Aug. 28, 2007, 8 pages.
U.S. Appl. No. 10/374,000, Office Action, mailed Feb. 13, 2006, 7 pages.
U.S. Appl. No. 10/374,000, Office Action, mailed Feb. 28, 2007, 8 pages.
U.S. Appl. No. 10/374,000, Office Action, mailed May 20, 2009, 9 pages.
U.S. Appl. No. 10/374,000, Response to Office Action, filed Dec. 28, 2006, 9 pages.
U.S. Appl. No. 10/374,000, Response to Office Action, filed Jun. 20, 2008, 8 pages.
U.S. Appl. No. 10/374,000, Response to Office Action, filed Mar. 30, 2009, 11 pages.
U.S. Appl. No. 10/374,000, Response to Office Action, filed May 12, 2006, 7 pages.
U.S. Appl. No. 10/374,000, Response to Office Action, filed May 29, 2007, 2006, 11 pages.
U.S. Appl. No. 10/374,000, Response to Office Action, filed Oct. 31, 2007, 8 pages.
U.S. Appl. No. 10/374,000. Office Action, mailed Jul. 28, 2006, 8 pages.
U.S. Appl. No. 10/374,000. Office Action, mailed Sep. 30, 2008, 7 pages.
U.S. Appl. No. 10/374,000, Office Action, mailed Mar. 20, 2008, 6 pages.
U.S. Appl. No. 11/320,223, Office Action, mailed Feb. 13, 2008, 11 pages.
U.S. Appl. No. 11/320,223, Office Action, mailed Jan. 21, 2010, 8 pages.
U.S. Appl. No. 11/320,223, Office Action, mailed Sep. 18, 2008, 7 pages.
U.S. Appl. No. 11/368,954, Interview Summary Communication from the USPTO, mailed May 12, 2010, 3 pages.
U.S. Appl. No. 11/368,954, Preliminary Amendment, filed Dec. 19, 2007, 9 pages.
U.S. Appl. No. 11/380,124, Office Action, dated Apr. 26, 2010, 7 pages.
U.S. Appl. No. 11/380,124, Office Action, dated Sep. 21, 2009, 8 pages.
U.S. Appl. No. 11/380,124, Office Action, mailed Jan. 16, 2009, 10 pages.
U.S. Appl. No. 11/380,621, Office Action, dated Jan. 14, 2010, 17 pages.
U.S. Appl. No. 11/380,621, Office Action, dated Jul. 1, 2009, 16 pages.
U.S. Appl. No. 11/380,621, Office Action, dated Jun. 6, 2008, 16 pages.
U.S. Appl. No. 12/023,280, Office Action, dated Jul. 23, 2009, 11 pages.
U.S. Appl. No. 12/023,280, Office Action, dated Oct. 5, 2009, 9 pages.
U.S. Appl. No. 12/143,377, Office Action, dated Feb. 4, 2010, 15 pages.
U.S. Appl. No. 12/143,377, Office Action, dated Sep. 13, 2010, 17 pages.
U.S. Appl. No. 12/143,377, Office Action, mailed Oct. 19, 2009, 9 pages.
U.S. Appl. No. 12/143,377, Response filed Jan. 13, 2011 (17 pages).
U.S. Appl. No. 12/143,377, Response, dated Aug. 27, 2009, 7 pages.
U.S. Appl. No. 12/143,377, Response, filed Jan. 19, 2010, 15 pages.
U.S. Appl. No. 12/143,377, Response, filed Jul. 6, 2010, 14 pages.
U.S. Appl. No. 12/175,182, Office Action, dated Feb. 22, 2010, 6 pages.
U.S. Appl. No. 12/175,182, Office Action, dated Jul. 22, 2010, 7 pages.
U.S. Appl. No. 12/175,182, Office Action, mailed Sep. 3, 2009, 7 pages.
U.S. Appl. No. 12/175,182, Response filed Jan. 24, 2011 (13 pages).
U.S. Appl. No. 12/175,182, Response, filed Dec. 3, 2009, 13 pages.
U.S. Appl. No. 12/175,182, Response, filed Jun. 22, 2010, 14 pages.
U.S. Appl. No. 12/175,270, Office Action dated Jan. 5, 2011 (6 pages).
U.S. Appl. No. 12/419,957, Office Action, dated Jun. 30, 2009, 6 pages.
U.S. Appl. No. 12/419,957, Office Action, mailed Feb. 18, 2010, 6 pages.

* cited by examiner

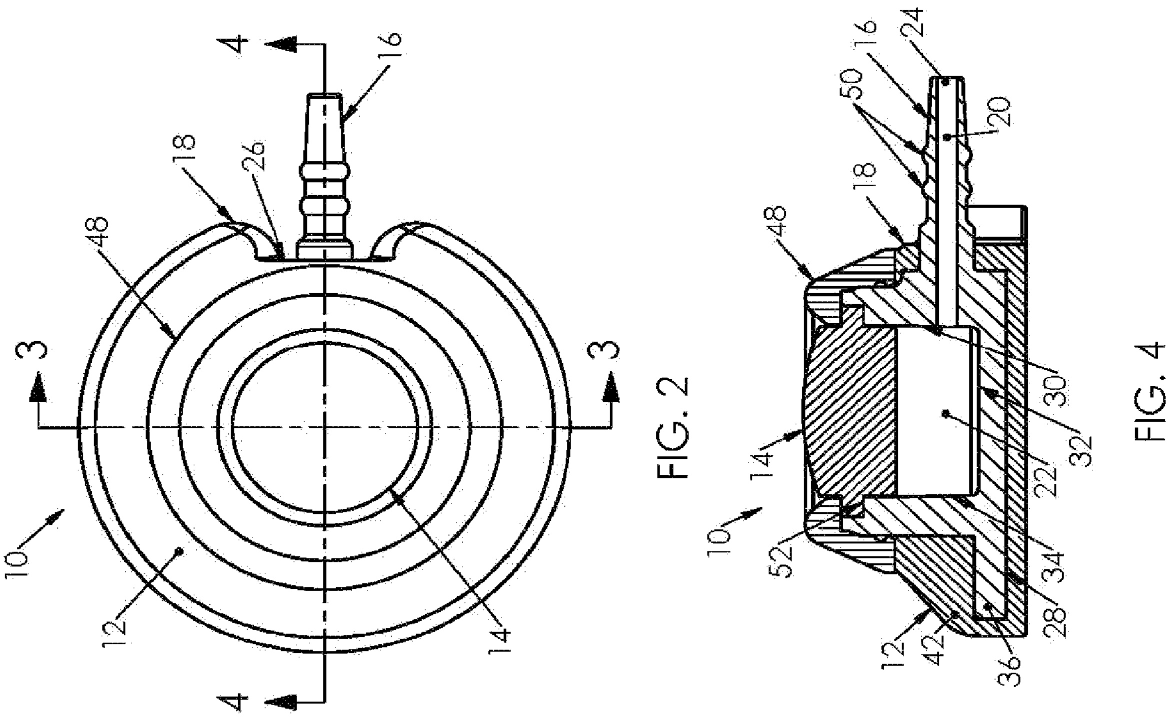
FIG. 2
FIG. 4
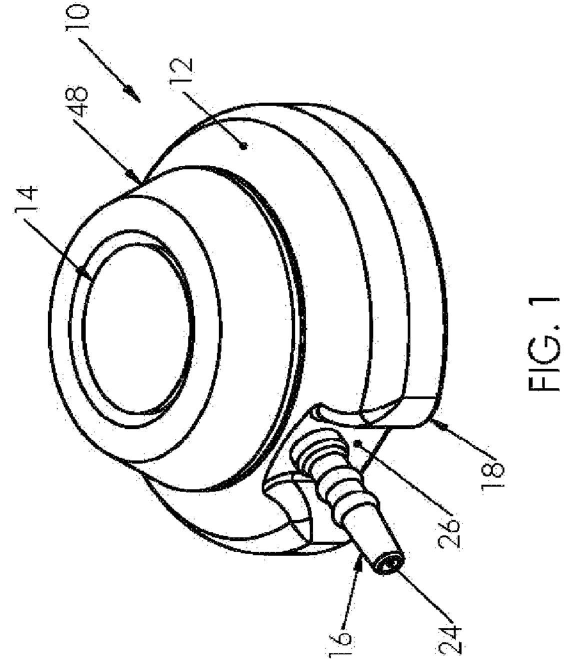
FIG. 1
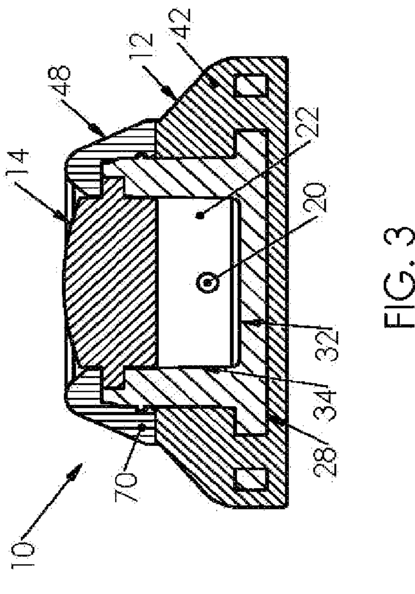
FIG. 3

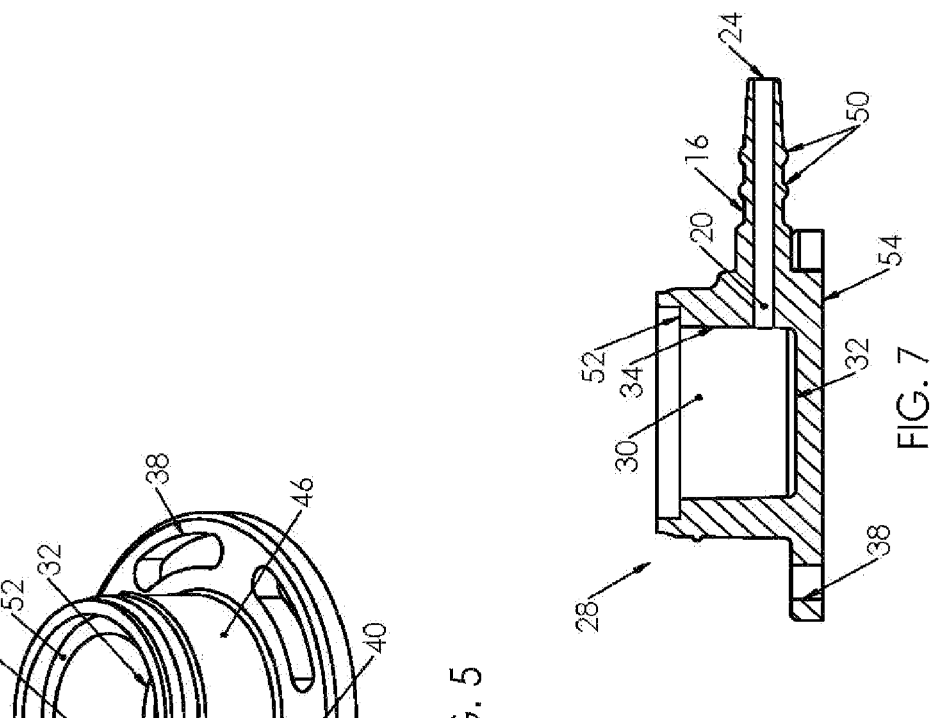
FIG. 5
FIG. 7
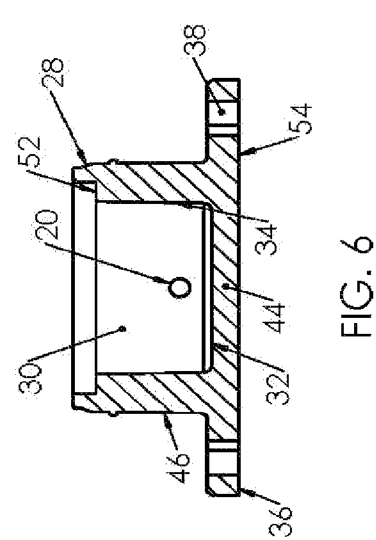
FIG. 6

16
56
40
28
38
30, 22
36
66
62
64
70
CT 16
56
28
36
66
60
62
64
70
54
CT 16
56
28
70
54
66
60
62
64
CT 16
72
12
40
36
38
32
34
28
74
12
40
32
34
28

16
40
72
28
32
34
30
36
38

16
40
74
28
32
34
30
36

VENOUS ACCESS PORT WITH MOLDED AND/OR RADIOPAQUE INDICIA

RELATED APPLICATIONS

This application is a continuation of, and claims the benefit of, co-pending U.S. patent application Ser. No. 17/865,449, filed Jul. 15, 2022, which is a continuation of U.S. patent application Ser. No. 16/035,879, filed Jul. 16, 2018, now U.S. Pat. No. 11,406,808, which is a divisional of U.S. patent application Ser. No. 15/350,273, filed Nov. 14, 2016, now U.S. Pat. No. 11,478,622, which is a continuation of U.S. patent application Ser. No. 13/550,745, filed Jul. 17, 2012, now U.S. Pat. No. 9,533,133, which is a continuation of U.S. patent application Ser. No. 12/143,377, filed Jun. 20, 2008, now U.S. Pat. No. 8,257,325, which claims the benefit of U.S. provisional application No. 60/936,491, filed Jun. 20, 2007, which applications are incorporated herein by reference.

FIELD OF THE INVENTION

This invention relates generally to medical devices, and more particularly to venous access ports having integrally molded and/or radiopaque indicia.

BACKGROUND OF THE INVENTION

Venous access ports for the infusion and/or withdrawal of fluids from a patient are well-known, secured to the proximal end of an implanted catheter. These ports are typically used for drug infusion or for withdrawal of small amounts of blood, where large flows of fluid are not required. The ports are assemblies of a needle-impenetrable housing with a discharge port in fluid communication with a catheter and a reservoir within the port housing, and provide as subcutaneous self-sealing septum that defines an access site for multiple needle sticks through the covering skin tissue of the patient, through the septum, and into the reservoir, without the need to continuously search for new access sites. Examples of such ports are disclosed, for example, in U.S. Pat. Nos. 4,704,103; 4,762,517; 4,778,452; 5,185,003; 5,213,574; and 5,637,102.

It is desired to provide a venous access port assembly that provides a medical practitioner with the capability to discern an important property of the port assembly after the port assembly has been implanted into a patient.

BRIEF SUMMARY OF THE INVENTION

The present invention is directed to an implantable venous access port having a marking visible by X-ray examination, providing identification on the X-ray of characteristics of the implanted access port. These characteristics might otherwise be unknown once the port is implanted under the skin of the patient. Considering that X-ray examination is normal practice prior to medical access of the port, an X-ray examination that also identifies important characteristics of an implanted port is beneficial to the practitioner.

Accordingly, one aspect of the present invention is the incorporation of a molded marking into or onto the venous access port, or the addition of radiopaque indicia onto the access port, and/or the addition of radiopaque indicia onto a molded marking integrated into the access port, all of which would be discernable under X-ray examination to provide information concerning a characteristic or attribute of the venous access port, so that a practitioner, subsequent to implantation of the access port under the skin of a patient, can determine that characteristic or attribute of the port by X-ray examination.

One such characteristic could be power injectable capability; that is, an indication that the venous access port is rated for the power injection of contrast fluid. Power injection capability can be indicated with the letters "CT," for "computed tomography," or "contrast enhanced computed tomography." "CT" would indicate the access port's capability to withstand high pressures used during injection of contrast fluid into a patient, and the letters "CT" would be understood in medical practice to indicate that the port is suitable for the high pressure injection of contrast fluid. Naturally, any characteristic or attribute of the venous access port could be indicated, and any choice of letters or symbols could be employed.

In one embodiment, an access port of the present invention includes a housing and a septum, providing an interior reservoir and a passageway extending from the reservoir through a stem of a discharge port to establish fluid communication with a proximal end of a catheter lumen to which the port assembly is secured prior to placement of the assembly into a patient. The port may optionally have more than one reservoir and associated septum. The housing could include molded therein the letters "CT." If the housing is made of a plastic material, such as a silicone elastomer the letters "CT" (or the entire housing) could be loaded with a radiopaque agent, allowing the letters "CT" (or the cadre housing to be seen by X-ray examination. If the housing comprises a metal material, or if the portion of the housing including the letters "CT" is made of a metal material, the letters would naturally be visible by X-ray examination.

BRIEF DESCRIPTION OF THE DRAWINGS

The accompanying drawings, which are incorporated herein and constitute part of this specification, illustrate the presently preferred embodiments of the invention, and together with the general description given above and the detailed description given below, serve to explain the features of the invention. In the drawings;

FIG. 1 is an isometric view of one embodiment of a venous access port of the present invention;

FIG. 2 is a pan view of the port FIG. 1;

FIGS. 3 and 4 are cross-sectional views of the port of FIGS. 1 and 2 taken along lines 3-3 and lines 4-4 of FIG. 2, respectively;

FIG. 5 is an isometric view of a needle-impenetrable housing base of the venous access port of FIG. 1;

FIGS. 6 and 7 are transverse cross-sectional and longitudinal cross-sectional views of the housing base of FIG. 5;

DETAILED DESCRIPTION OF THE INVENTION

Figures 8, 9, 10:
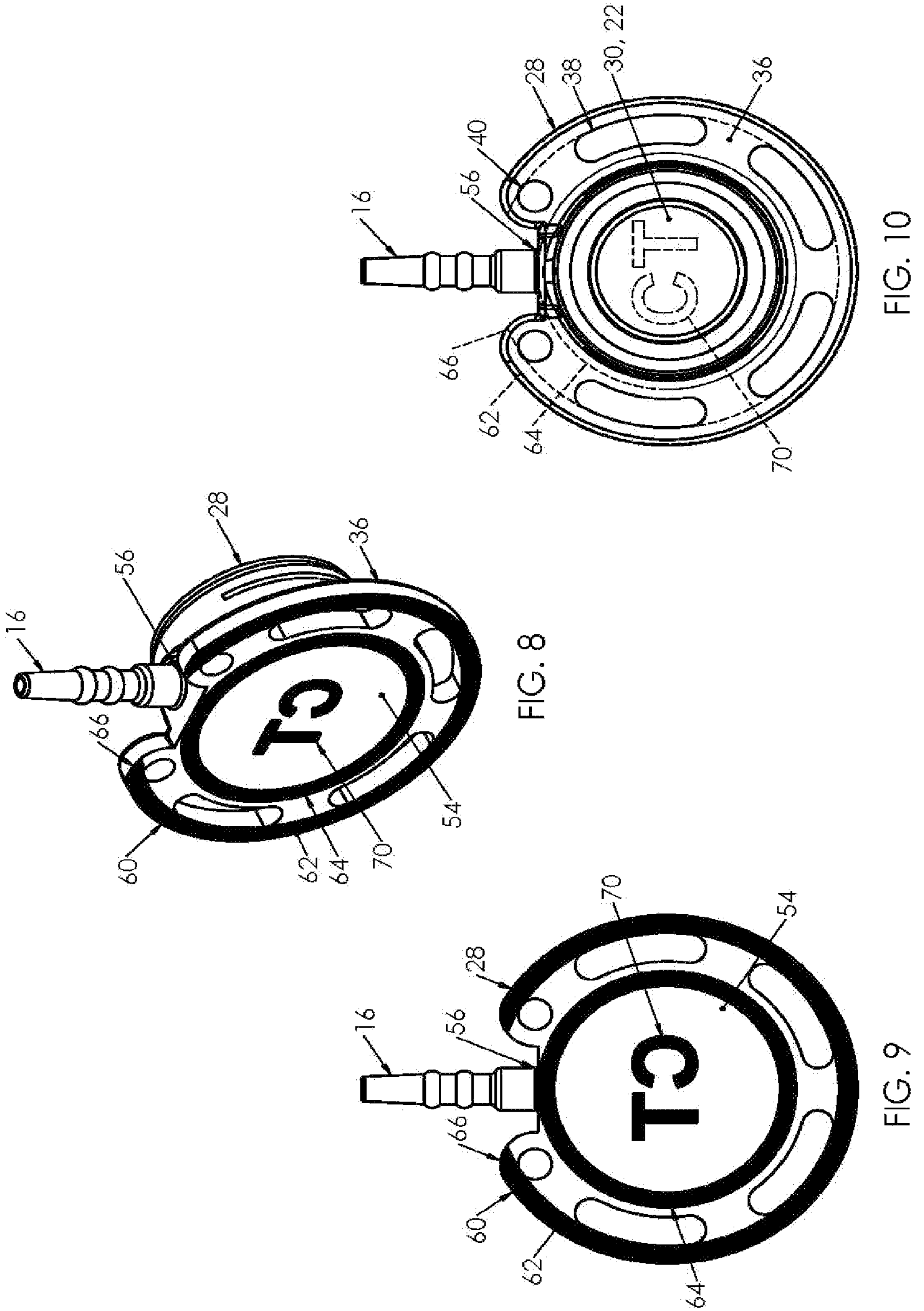
FIG. 8 is an isometric view from below of one embodiment of the housing base of FIG. 5, showing radiopaque indicia applied on the housing base bottom surface.
FIGS. 9 and 10 are bottom and top views of the housing base of FIG. 8 having radiopaque indicia thereon, with the top view (FIG. 10) being analogous to a X-ray view of the venous access port seen by a radiologist, with indicia visible by X-ray shown by dashed lines in FIG. 10.

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof, and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 to 4 includes a housing 12 and a septum 14, with a discharge port 16 extending from a distal end 18 of the port assembly 10 to be attached securely and sealingly to the proximal end of a catheter (not shown). A passageway 20 extends from the interior reservoir 22 to the distal tip opening 24 of discharge port 16. A recess 26 is seen to be provided along both sides of discharge port 16, facilitating insertion of the discharge port 16 into the catheter lumen and providing a clearance for a locking sleeve or clamp (not shown) utilized to compress the catheter lumen wall against the exterior surface of the discharge port 16 for assured sealed connection of the catheter with the port assembly 10.

With reference now to FIGS. 3 to 7, the interior of the port assembly 10 is shown to provide an interior reservoir 22. Housing 12 is shown to include a housing base 28 of needle-impenetrable material that includes a web 30 having a bottom boor 32 and side walls 34 that define the interior reservoir 22 beneath septum 14. Bottom floor 32 may be convex or elevated (not shown) toward the center of the reservoir, if desired. Housing base 28 includes a base flange 36 extending radially outwardly from the bottom of well 30, and base flange 36 includes openings 38, 40 that serve to enable suturing to the patient upon placement of the venous access port and the attached catheter into the patient.

As shown in FIGS. 3 and 4, a skirt 42 is overmolded about housing base 28 and may be of silicone elastomer. It is seen that skirt 42 encapsulates the outer surfaces of the bottom wall 44 and the bottom portion of the side walls 46 of housing base 28, and is shown to fill in the suture holes 38, 40; but since the material is silicone elastomer, suturing is possible since the suturing needle can easily be inserted through the material of skirt 42 and through the suture holes, and thereafter the filled openings provide minimal opportunity for ingrowth of patient tissue into the openings.

Also seen in FIGS. 1 to 4 is cap 48, which secures to housing base 28 to in turn secure septum 14 in position in the port assembly 10. Preferably, skirt 42 is insert molded onto base flange 36 of housing base 28 after cap 48 is secured to the upper portion of housing base 28 to secure the septum in position. It is seen in FIGS. 4 and 7 that discharge port 16 is integral with housing base 28 as is preferable. Discharge port 16 is shown to have a pair of annular ridges 50 that facilitate with the mechanical connection of the catheter proximal end with the port assembly 10. Housing base 28 includes a septum seat 52 extending into the top of well 30, into which a flange of the septum will be seated, preferably under radially inward compression. Housing base 28 has a bottom outer surface 54.

Radiopaque markings 60 of the present invention are shown in FIGS. 8 to 10. A larger outer circle 62 is seen provided on the outermost periphery of bottom base surface 54, and a smaller inner circle 64 is seen provided within the area circumscribed by the suture openings 38 and holes 40 through base flange 36. Adjacent to discharge port 16, a recess 56 is provided in the skirt of the housing base to provide a clearance for use of a connection sleeve that will be used to secure the catheter (not shown), and outer circle 62 is shown to have a gap 66 at the recess. Outer and inner circles or rings 62, 64 circumscribe radiopaque indicia 70.

Radiopaque indicia 70 are provided on bottom outer surface 54 within the region directly beneath the reservoir and septum. In the example shown, indicia 70 comprise the letters "CT" (FIG. 10) representing the term "computed tomography." The meaning of this particular example of indicia is that the venous access port assembly 10 is rated for high pressure injection such as is necessary for infusion into the patient of contrast medium that is used in computed tomography. Other indicia may of course be used that indicate some other attribute or characteristic of the venous access port assembly. The radiopaque markings and indicia would appear on an X-ray of the patient, and the indicia are provided in a mirror-image orientation on the bottom outer surface of the housing base (FIGS. 7 and 8) so that the indicia would appear as "CT" when the X-ray is viewed (FIG. 9), easily discerned by the radiologist or technologist. Centering of the indicia within the region (identified as "30, 22" in FIG. 10) directly beneath the reservoir and septum minimizes any obscuring by the structure of the venous access port assembly, and the indicia may also be easily discernable should the port assembly be at an angle from the horizontal plane of the X-ray; the outer and inner circles 62, 64 would appear oval or elliptical should the port assembly be at such an angle. Gap 66 in outer circle 62 would also appear and would indicate the location of the discharge port stem 16, The radiopaque markings may constitute marking fluid that is embossed or imprinted or otherwise applied onto the surface of the housing base 28, such as black radiopaque ink Part No. C11002 Rev A formulated by Creative Imprinting of Erie, Pa., from Marabu Tampapur TPU 910 clear with tungsten added, available from Marabuwerke GmbH & Co. KG of Stuttgart, Germany, and may be applied on plasma-treated surfaces. At least the housing base 28, the septum 14 and the skirt 42 are of radiotransparent or radiolucent material as is well known in implanted medical devices, and the housing base may be molded of polysulfone resin.

The radiopaque markings may alternatively applied to the inwardly facing surface of the bottom wall of the housing base, or may constitute foil or film (such as a decal) of radiopaque material embedded within the housing base, these alternatives not being shown in the drawings.

Figure 11:
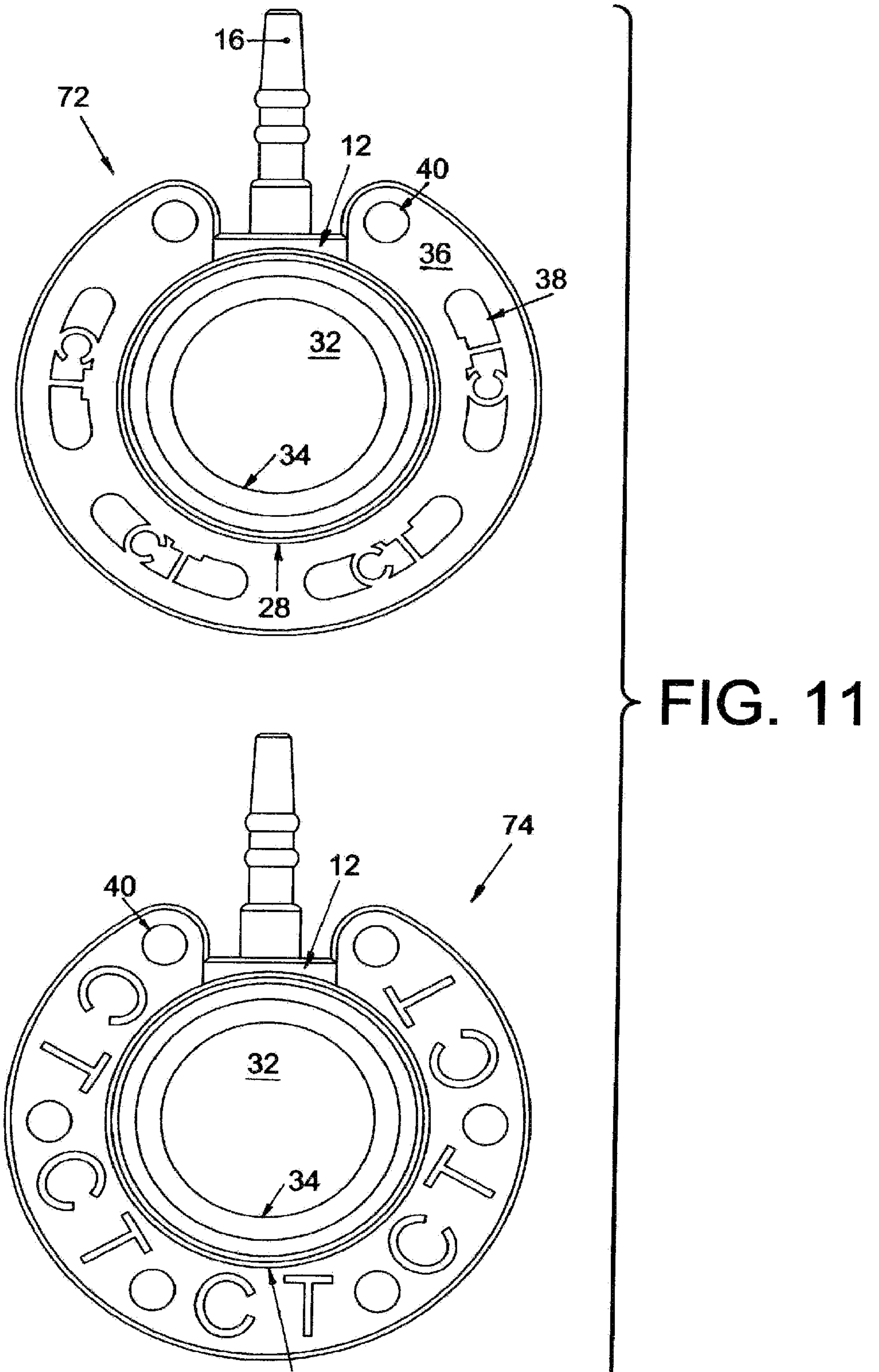
FIG. 11 illustrates top views of two alternative embodiments of the needle-impenetrable housing base of the venous access port of FIG. 1, showing integrally molded "CT" markings.
Figures 12, 13:
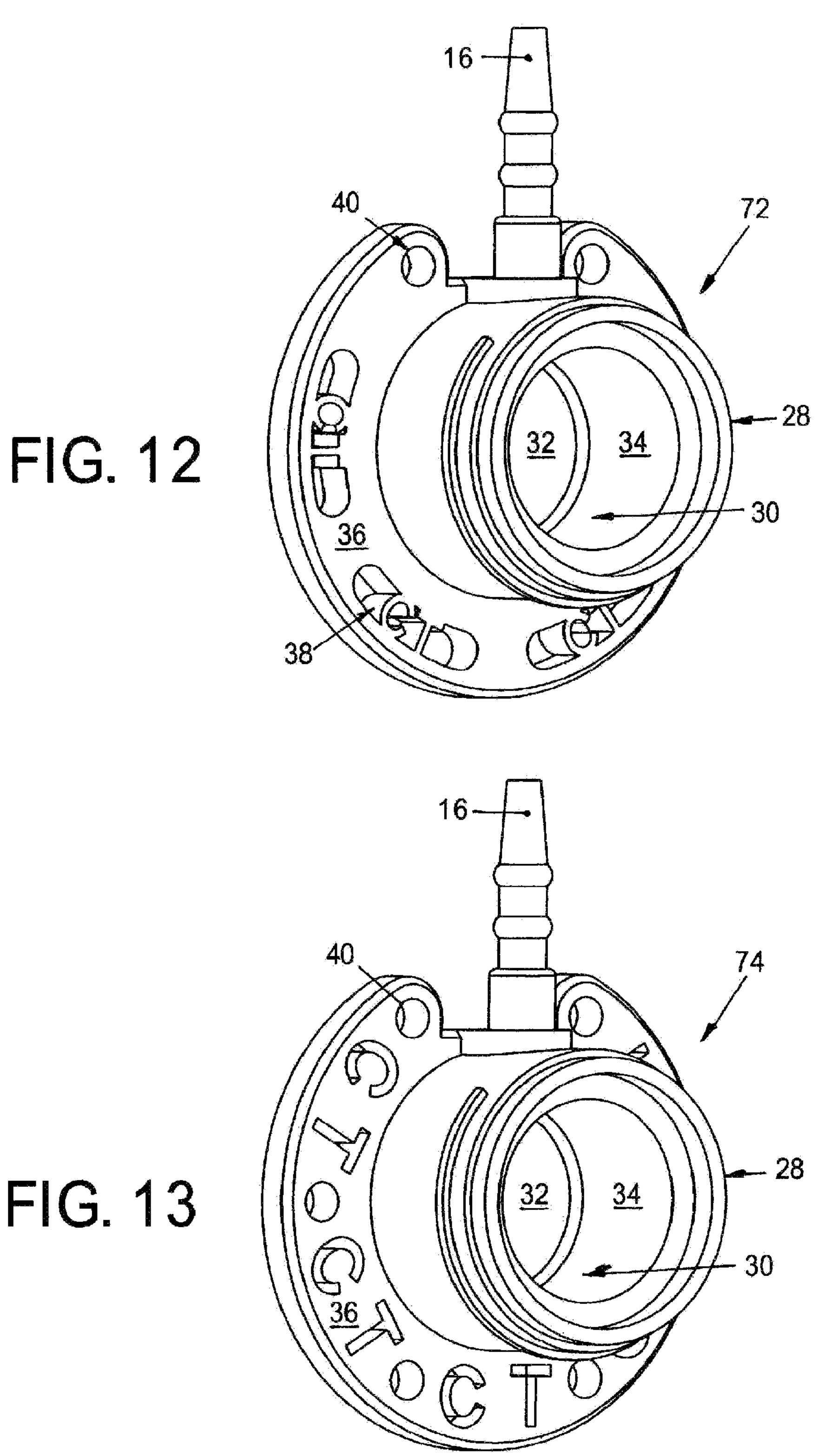
FIG. 12 illustrates an isometric view of one of the FIG. 11 embodiments of the needle-impenetrable housing base of the venous access port of FIG. 1, featuring an integrally molded "CT" marking where the letters "CT" are formed of housing material.
FIG. 13 illustrates an isometric view of the other of the FIG. 11 embodiments of the needle-impenetrable housing base of the venous access port of FIG. 1, featuring an integrally molded "CT" marking where the letters "CT" comprise voids in the housing material, as if cut or punched out of the housing material.

FIG. 11 illustrates top views of two alternative embodiments 72, 74 of the needle-impenetrable housing base 28 of the venous access port 10 of the present invention. Each of the alternative embodiments 72, 74 shows "CT" markings integrally formed in the base flange 36 of the housing base 28. The first alternative embodiment 72, an isometric view of which is illustrated in FIG. 12, features integrally molded "CT" markings within the suture openings 38, where the letters "CT" are formed of the base flange 36 material. The second alternative embodiment 74, an isometric view of which is illustrated in FIG. 13, features integrally molded "CT" markings alongside the suture openings 38, 40, where the markings are voids in the base flange 36 material, as if cut or punched out of the base flange 36 material. Naturally, the markings could be configured elsewhere within or about the housing base 28, or within a peripheral portion of another component of the venous access port 10.

If the housing base 28 is made of a plastic material, such as a silicone elastomer or polysulfone resin, the letters "CT," or the base flange 36, or the entire housing base 28, could be applied with a radiopaque agent or fluid, allowing the applied area to be visible by X-ray examination. If the housing base 28 is comprised of a metal material, or if the base flange 36, or a portion thereof, is comprised of metal (particularly the letters "CT"), those portions would naturally be visible by X-ray examination without application of the radiopaque agent.

It will be appreciated by those skilled in the art that changes could he made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A venous access port assembly for implantation into a patient, the venous access port assembly comprising:

a needle-penetrable septum;

a housing comprising a housing base at least partially defining at least one reservoir; and a bottom surface, the bottom surface comprising one or more X-ray discernable indicia at least partially cut or punched out of the bottom surface and wherein the one or more X-ray discernable indicia are shaped as letters or symbols provided in mirror-image orientation on the bottom surface and comprise the letters "C" and "T" in mirror-image orientation, wherein the one or more X-ray discernable indicia are visible under X-ray examination when the assembly is subcutaneously implanted in a patient and indicate an orientation of the venous access port assembly after implantation and wherein the venous access port assembly is capable of withstanding pressures used during power injection of contrast fluid.

2. The venous access port assembly of claim 1, wherein the bottom surface includes a bottom surface of a base flange.

3. The venous access port assembly of claim 2, wherein the venous access port assembly is comprised at least partially of a radiopaque material.

4. The venous access port assembly of claim 3, wherein the one or more X-ray discernable indicia are voids in the bottom surface of the base flange.

5. The venous access port assembly of claim 4, wherein the bottom surface is comprised at least partially of the radiopaque material.

6. The venous access port assembly of claim 5, wherein the one or more X-ray discernable indicia extend completely through the radiopaque material.

7. The venous access port assembly of claim 1, wherein the housing further comprises a cap.

8. The venous access port assembly of claim 1, further comprising a radiotransparent or radiolucent skirt over molded about at least a portion of the housing.

9. The venous access port assembly of claim 1, wherein the one or more X-ray discernable indicia are at least partially within a region directly beneath the reservoir and septum.

10. The venous access port assembly of claim 1, wherein the one or more X-ray discernable indicia are directly beneath the reservoir and septum.

11. A venous access port assembly for implantation into a patient, the venous access port assembly comprising:

a housing having a base of needle-impenetrable material that includes a well having a bottom floor, and side walls that define an interior reservoir, the housing further having a discharge port extending from the reservoir;

a needle-penetrable septum communicating with the housing, the reservoir being beneath the septum; and a marking indicating a characteristic of the assembly and in the shape of letters comprising the letters "CT" in mirror-image orientation;

wherein the marking is in a bottom surface of said housing wherein the letters "CT" are at least partially embedded within said bottom surface, the marking being visible by X-ray examination when the assembly is subcutaneously implanted in a patient and the marking indicates an orientation of the venous access port assembly after implantation, and wherein the venous access port is capable of withstanding pressures used during power injection of contrast fluid.

12. The venous access port assembly of claim 11, wherein the housing comprises metal material.

13. The venous access port assembly of claim 11 wherein the bottom floor is convex or elevated toward a center of the reservoir.

14. The venous access port assembly of claim 11, wherein the base includes a septum seat.

15. The venous access port assembly of claim 14, wherein the septum seat extends to a top of the well.

16. The venous access port assembly of claim 11, wherein the venous access port assembly is at least partially comprised of radiotransparent material.

17. The venous access port assembly of claim 11, wherein the bottom floor further includes suture openings.

18. The venous access port assembly of claim 11, wherein at least a portion of said marking is provided within a region directly beneath the reservoir and septum.

19. A venous access port assembly for implantation into a patient, the venous access port assembly comprising:

a housing having a base of needle-impenetrable material that includes a well having a bottom floor, side walls that define an interior reservoir and a discharge port extending from the reservoir;

a needle-penetrable septum communicating with the housing, the reservoir being beneath the septum; and a marking indicating a characteristic of the assembly;

wherein the marking is formed in the bottom floor, the marking being visible by X-ray examination when the assembly is subcutaneously implanted in a patient and being in the shape of letters "CT" in mirror-image orientation, and wherein the venous access port is capable of withstanding pressures used during power injection of contrast fluid.

* * * * *